(12) United States Patent
Monguillon et al.

(10) Patent No.: US 9,994,544 B2
(45) Date of Patent: Jun. 12, 2018

(54) METHOD FOR PREPARING TRIOXANE

(71) Applicant: Arkema France, Colombes (FR)

(72) Inventors: Bernard Monguillon, Bayonne (FR); Jean-Alex Laffitte, Pau (FR)

(73) Assignee: Arkema France, Colombes (FR)

( * ) Notice: Subject to any disclaimer, the term of this patent is extended or adjusted under 35 U.S.C. 154(b) by 0 days. days.

(21) Appl. No.: 15/502,098

(22) PCT Filed: Jul. 17, 2015

(86) PCT No.: PCT/FR2015/051968
§ 371 (c)(1),
(2) Date: Feb. 6, 2017

(87) PCT Pub. No.: WO2016/020592
PCT Pub. Date: Feb. 11, 2016

(65) Prior Publication Data
US 2017/0233366 A1    Aug. 17, 2017

(30) Foreign Application Priority Data

Aug. 7, 2014  (FR) ...................... 14 57676

(51) Int. Cl.
*C07D 323/06* (2006.01)

(52) U.S. Cl.
CPC ................. *C07D 323/06* (2013.01)

(58) Field of Classification Search
CPC .................................................. C07D 323/06
See application file for complete search history.

(56) References Cited

U.S. PATENT DOCUMENTS 3,483,214 A    12/1969  Sperber et al.
2006/0058537 A1    3/2006  Haubs et al.

FOREIGN PATENT DOCUMENTS

| FR | 1549133 A | 12/1968 |
| GB | 949145 | 2/1964 |
| GB | 1064013 | 4/1967 |
| WO | 9515960 A1 | 6/1995 |
| WO | 2013076286 A1 | 5/2013 |

OTHER PUBLICATIONS

International Search Report and Written Opinion for International Application No. PCT/FR2015/051968, dated Sep. 18, 2015, 9 Pages.

*Primary Examiner* — Timothy R Rozof
(74) *Attorney, Agent, or Firm* — RatnerPrestia

(57) ABSTRACT

The present invention concerns a method for preparing 1,3,5-trioxane by trimerization of formaldehyde in the presence of methanesulfonic acid. The invention also concerns the use of at least one catalyst comprising methanesulfonic acid for the trimerization of formaldehyde into 1,3,5-trioxane.

22 Claims, No Drawings

METHOD FOR PREPARING TRIOXANE

CROSS-REFERENCE TO RELATED APPLICATIONS

This is the national phase of International Application No. PCT/FR2015/051968, filed 17 Jul. 2015, which claims priority to French Application No. 1457676, filed 7 Aug. 2014. The disclosure of each of these applications is incorporated herein by reference in its entirety for all purposes.

FIELD OF THE INVENTION

The present invention relates to a process for preparing 1,3,5-trioxane (denoted hereinafter "trioxane") from formaldehyde in the presence of a specific acid catalyst allowing an improved yield and a high selectivity of trioxane while at the same time guaranteeing a considerable energy saving and a decrease in trioxane production costs.

BACKGROUND OF THE INVENTION

Trioxane is widely used in many industrial fields and, for example, as a starting product in the production of polyoxymethylene (POM). POMs have very good physical characteristics, including their high tensile strength and impact resistance, excellent dimensional stability, good electrical insulation characteristics and a wide working temperature range. Currently, POMs are used in many industries, such as the motor vehicle industry, the sports industry and the electronics industry.

Since the POM market is in full expansion, there is therefore a need to produce trioxane, which is a POM precursor, with a high yield and selectivity, in large amounts, as economically as possible and without harming the environment.

Trioxane is usually produced by trimerization of formaldehyde, according to well-known techniques. Generally, trioxane is formed from a more or less concentrated aqueous solution of formaldehyde, in the presence of acid catalyst at high temperatures. The trioxane is then separated from the reaction medium by distillation. The synthesis vapor, which, in addition to the trioxane, still contains formaldehyde, water and reaction by-products, can be rectified in an enrichment column. The trioxane-rich fraction obtained is then subjected to extraction and/or any separation method known to those skilled in the art.

For example, it is possible to directly carry out the extraction of the trioxane after distillation thereof using a water-immiscible extraction agent. The extraction, which makes it possible to recover the trioxane in the extraction agent, is generally followed by distillation of the organic phase, which makes it possible to obtain trioxane which is pure, or at the very least of very high purity.

However, the methods known to those skilled in the art still suffer from numerous drawbacks and the improvements proposed have not actually made it possible to further improve or to optimize the trioxane preparation process.

Document GB949145 describes the preparation of trioxane from formaldehyde in aqueous solution in the presence of strong inorganic acids, for example sulfuric acid, perchloric acid and phosphoric acid, or of strong organic acids, such as aromatic sulfonic acids, particularly benzenesulfonic acid and homologs thereof, for example para-toluenesulfonic acid. Only sulfuric acid is exemplified in said document.

Document US2006/0058537 describes a process for preparing trioxane in the presence of catalysts. The catalysts are strong acids, for example sulfuric acid, trifluoromethanesulfonic acid or toluenesulfonic acid, or very acidic ion exchangers. It is also possible to use acidic zeolithes or heteropolyacids. Again in said document, only sulfuric acid is exemplified.

Document FR1549133 describes a process for preparing trioxane in the presence of acid catalysts. Among these acids, sulfuric acid is preferably used and, for example, phosphoric acid can be used. Other examples of catalysts are acidic salts, such as potassium hydrogen sulfate or zinc chloride, aliphatic and aromatic sulfonic acids, such as p-toluenesulfonic acid or 1,5-naphthalenedisulfonic acid or else acidic ion exchangers, for example commercial cation exchange resins bearing $SO_3H$ radicals. Only sulfuric acid is exemplified.

Document WO2013/076286 describes a process for preparing trioxane in the presence of various acid catalysts and in an aprotic solvent. However, a step of preparing formaldehyde in an aprotic solvent lengthens the duration of the process. Furthermore, this additional step requires modifying the already existing industrial equipment. Preferably, the catalysts used are Brønsted acids and Lewis acids. The catalyst is preferably chosen from the group consisting of trifluoromethanesulfonic acid, perchloric acid, methanesulfonic acid, toluenesulfonic acid and sulfuric acid or derivatives thereof, such as the anhydrides or esters, or any other derivative which generates the corresponding acid. Lewis acids such as boron trifluoride or arsenic pentafluoride can also be used. It is also possible to use a mixture of catalysts mentioned above. In the examples, sulfuric acid, trifluoromethanesulfonic acid, perchloric acid and a sulfolane ion exchange resin are used.

Document GB1064013 describes a process for preparing trioxane in the presence of an acidic emulsifier comprising one or more alkylsulfonic or arylalkylsulfonic or alkylarylsulfonic or arylsulfonic acids with one or more sulfonic acid functions. Preferably, the alkyl groups of the alkylsulfonic acids contain from 14 to 16 carbon atoms. Only said $C_{14}$-$C_{16}$ alkylsulfonic acids are exemplified.

Various catalysts, inorganic acids and organic acids have been mentioned, such as para-toluenesulfonic acid. However, it has the drawback of being in solid form at ambient temperature, thus requiring a step of dilution in a solvent. Moreover, only sulfuric acid, trifluoromethanesulfonic acid, perchloric acid and a sulfolane ion exchange resin are exemplified.

Although several acid catalysts have been mentioned in the prior art documents, and in particular the prior art documents mentioned above, sulfuric acid is at the current time the acid catalyst most widely used for the preparation of trioxane. Nevertheless, sulfuric acid has the drawback of being corrosive and of generating by-products which result in a significant loss of trioxane production yield. Indeed, the principal side reactions involved are:

the dismutation of formaldehyde ($CH_2O$) in the presence of water ($H_2O$) to give formic acid (HCOOH) and methanol ($CH_3OH$), (Cannizzaro reaction), according to the following scheme:

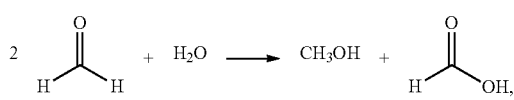

and the following equilibrated reaction, resulting in the formation of methyl formate ($HCOOCH_3$) from the formic acid and methanol previously formed:

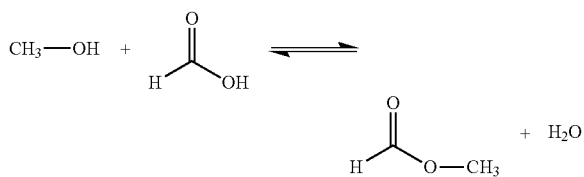

It is also possible to observe the following side reaction which generates methanol and carbon dioxide ($CO_2$):

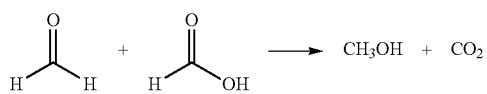

and also, in an acidic medium, the formation of glycolic acid ($HOCH_2COOH$):

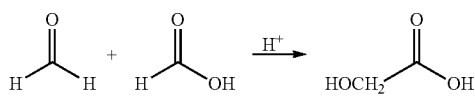

BRIEF SUMMARY OF THE INVENTION

There is therefore still a need to have available a simple, reliable, economical and environmentally friendly source for the preparation of formaldehyde which does not require major industrial modifications. There is thus a need to have available a process which makes it possible to improve the trioxane yield and selectivity compared with the methods known to those skilled in the art; a process which also allows a significant decrease in or elimination of by-products. Finally, there is a need to have available a process for preparing formaldehyde using an acid catalyst that is less harmful to the environment, compared with the acid catalysts generally used.

The present invention has many advantages and in particular makes it possible to totally or at least partially overcome the drawbacks presented above. Other further advantages will emerge in the light of the description of the invention which follows.

The invention thus relates to a simple, efficient and economical process which makes it possible to have available a source of formaldehyde in the form of trimerized formaldehyde. According to a first aspect, the invention relates to a process for the trimerization of formaldehyde, and more specifically a process for preparing trioxane from formaldehyde, said process comprising at least the following steps:

1) bringing formaldehyde into contact with a catalyst comprising at least methanesulfonic acid;
2) carrying out a reaction of trimerization of said formaldehyde into trioxane; and
3) separating the trioxane from the reaction medium.

According to a second aspect, a subject of the present invention is the use of a catalyst comprising methanesulfonic acid for trimerizing formaldehyde, and in particular for preparing trioxane.

A subject of the present invention is also the use of a catalyst comprising methanesulfonic acid for increasing the formaldehyde trimerization yield, and more particularly for producing trioxane.

Finally, a subject of the present invention is the use of a catalyst comprising methanesulfonic acid for increasing the trioxane selectivity during the formaldehyde trimerization.

DETAILED DESCRIPTION OF CERTAIN EMBODIMENTS OF THE INVENTION

It has in fact been discovered, surprisingly, that the use of a catalyst comprising methanesulfonic acid as acid catalyst in an aqueous medium makes it possible to improve in particular the formaldehyde trimerization reaction yield, the trioxane yield and the trioxane selectivity. Moreover, the catalyst comprising methanesulfonic acid is less harmful to the environment than the acid catalysts generally used for formaldehyde trimerization.

Unless otherwise mentioned, the percentages of material that are mentioned are percentages by weight.

The term "reaction mixture" is intended to mean the mixture comprising all the starting reagents. The term "reaction medium" is intended to mean the mixture comprising all the products formed during the formaldehyde trimerization reaction, and also all the reagents present at the beginning of the reaction and the unreacted reagents.

A subject of the invention is thus a process for the trimerization of formaldehyde, and more particularly for preparing trioxane as defined above.

Advantageously, the formaldehyde trimerization process comprises at least steps 1) to 3) as indicated previously.

The trioxane formation step 2) is carried out by means of a formaldehyde trimerization reaction in the presence of at least one catalyst comprising methanesulfonic acid. The reaction of trimerization of formaldehyde into trioxane can be represented by the following scheme:

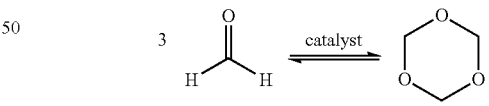

This trioxane formation step is preferably carried out in an aqueous medium. However, it is also possible to carry it out in an organic, preferably protic organic, more preferably polar protic organic, solvent medium or even in an aqueous-organic solvent medium, that is to say in a water/organic solvent mixture, said organic solvent preferably being as defined above. The best results in terms of yield, selectivity and environmental protection have however been obtained by carrying out the process of the invention in an aqueous medium, and advantageously in the absence of organic solvent.

The formaldehyde (raw material) can be used in any form known to those skilled in the art, for example and usually either in aqueous solution or in solid form, which then corresponds to the form known as paraformaldehyde. The two principal sources of solid formaldehyde are paraformaldehyde (formaldehyde oligomers) and polyoxymethylenes (formaldehyde polymers).

For the needs of the process of the invention, the formaldehyde is used in an aqueous solution. Advantageously, said aqueous solution comprises the formaldehyde, water and optionally additives. Advantageously, the formaldehyde content ranges from 30% to 90% by weight, limits included, relative to the total weight of the aqueous solution. Preferably, the formaldehyde content ranges from 30% to 70%, more preferably from 30% to 50% by weight, limits included, relative to the total weight of the aqueous solution. Even more preferentially, the formaldehyde content is approximately 40% by weight relative to the total weight of the aqueous solution.

In the reactor, the formaldehyde is introduced such that the formaldehyde content ranges from 30% to 90% by weight relative to the total weight of the reaction mixture. Preferably, the formaldehyde content ranges from 30% to 70% by weight relative to the total weight of the reaction mixture. More preferably, the formaldehyde content ranges from 30% to 60% by weight relative to the total weight of the reaction mixture. The preceding ranges are understood to include the limits included.

When the reaction mixture contains water, the latter can advantageously come from the aqueous solution comprising the formaldehyde, but also optionally from the catalyst in aqueous form as defined hereinafter, and also optionally from additives in aqueous solution as defined hereinafter. It is of course possible to add water and/or another solvent, for example an organic solvent, to the reaction mixture.

Advantageously, the water content in the reactor ranges from 70% to 10% by weight, limits included, relative to the total weight of the reaction mixture, preferably from 70% to 30% by weight relative to the total weight of the reaction mixture, more preferably from 70% to 50% by weight, limits included, relative to the total weight of the reaction mixture, and is for example equal to approximately 60% by weight relative to the total weight of the reaction mixture.

The reaction mixture optionally comprises additives such as antifoams, anticorrosion agents, surfactants, stabilizers, and the like. As previously indicated, the abovementioned additives can optionally be in the form of an aqueous solution.

The additive content in the reaction medium generally ranges from 0 to 15%, limits included, by weight relative to the total weight of the reaction mixture. Preferably, the additive content in the reaction mixture ranges from 1% to 10% by weight, limits included, relative to the total weight of the reaction mixture, and more preferably from 1% to 5% by weight, limits included, relative to the total weight of the reaction mixture.

It has been discovered, entirely surprisingly, that the use of at least one catalyst comprising methanesulfonic acid makes it possible to significantly increase the formaldehyde trimerization yield, or the trioxane formation yield, compared with the use of sulfuric acid which is the catalyst most commonly and widely used to prepare trioxane from formaldehyde. Moreover, the catalyst comprising methanesulfonic acid, by virtue of its non-oxidizing and biodegradable properties, makes the process less harmful to the environment than the known methods using sulfuric acid.

For the needs of the present invention, it is preferred to use a single catalyst comprising methanesulfonic acid. According to one preferred embodiment, the catalyst comprising methanesulfonic acid is an aqueous solution of methanesulfonic acid. However, it is possible to use anhydrous methanesulfonic acid, known as AMSA, this possibility being entirely suitable for a trioxane synthesis process using formaldehyde in an aqueous solution.

In another preferred embodiment, the process according to the present invention uses methanesulfonic acid in an aqueous solution as formaldehyde trimerization catalyst, which also offers the advantage of avoiding an additional step of dissolving the formaldehyde in water and/or in an organic solvent.

As previously indicated, the catalyst comprising methanesulfonic acid can be used in anhydrous form or in an aqueous solution. Preferably, the catalyst according to the invention is in a more or less dilute aqueous solution, said catalyst being diluted in water, optionally in the presence of additives.

Thus, when the catalyst comprises methanesulfonic acid in an aqueous solution, it can be used in concentrations which can range from 0.1% to 99.9% by weight of acid, limits included, preferably from 1% to 99% by weight, limits included, preferably from 30% to 95% by weight, limits included, relative to the total weight of the aqueous solution of methanesulfonic acid. Preferably, the methanesulfonic acid content ranges from 50% to 80% by weight relative to the total weight of the catalyst, and even more preferably the methanesulfonic acid content is 70% by weight relative to the total weight of the catalyst. For example, methanesulfonic acid (AMS) at 70% by weight in water is sold by the company ARKEMA.

In the reaction mixture, the catalyst comprising methanesulfonic acid in anhydrous form or in an aqueous solution is introduced such that the methanesulfonic acid content, expressed in anhydrous form, ranges from 0.1% to 25% by weight, limits included, relative to the total weight of the reaction mixture. Preferably, the methanesulfonic acid content ranges from 0.1% to 15% by weight relative to the total weight of the reaction mixture and more preferably from 2% to 10% by weight, limits included, relative to the total weight of the reaction mixture.

According to one embodiment, the catalyst comprising methanesulfonic acid can also comprise one or more other acids, preferably strong acids, more preferably strong inorganic acids, such as those normally used for the trioxane trimerization reaction, and, by way of nonlimiting examples, sulfuric acid, phosphoric acid, para-toluenesulfonic acid, benzenesulfonic acid, alkylsulfonic acids other than methanesulfonic acid, and mixtures of two or more thereof, in any proportions, and also any other acid catalyst capable of being used as catalysts for trimerization of formaldehyde into trioxane.

Preferably, when the catalyst comprises methanesulfonic acid and one or more other acid catalysts, the methanesulfonic acid weight content is greater than the amount of the other acid(s) present in the mixture, for example two or three times greater.

The trimerization step 2) is advantageously carried out by heating the reaction mixture comprising said at least one catalyst, the formaldehyde, a solvent, advantageously water, and the optional additives as described above. The reaction temperature generally ranges from 0° C. to 200° C., preferably from 50° C. to 150° C., more preferably from 70° C. to 140° C., and even more preferentially from 90° C. to 130° C.

The trimerization reaction can be carried out at atmospheric pressure, under pressure or under reduced pressure. Those skilled in the art will be able to adjust the pressure in particular according to the temperature and the concentration of formaldehyde in the reaction mixture. Generally, the pressure can be set between 0.1 and 10 bar (i.e. between $0.1 \cdot 10^5$ Pa and $10 \cdot 10^5$ Pa). Preferably, the pressure ranges from 0.1 to 5 bar (i.e. between $0.1 \cdot 10^5$ Pa and $5 \cdot 10^5$ Pa). The pressure in the reactor can be regulated such that it is between the limits indicated previously. Entirely preferably, the reaction is carried out at atmospheric pressure.

The formation of trioxane by trimerization of formaldehyde in the presence of at least one catalyst comprising methanesulfonic acid is carried out for the period of time required for the most complete conversion possible of the formaldehyde into trioxane. This period of time can range from a few minutes to several hours.

The trioxane formation step can be carried out with or without stirring, preferably with stirring. When there is stirring, it can be provided by any method known to those skilled in the art, for example a magnetic stirrer, a paddle stirrer, a propeller stirrer, or any other stirring method commonly used and known for this type of reaction.

Since the formaldehyde trimerization reaction is an equilibrated reaction, it is possible to shift the reaction equilibrium according to Le Chatelier's principle in order to promote trioxane formation. Thus, and according to one preferred embodiment of the invention, the trioxane formation can be greatly promoted, for example, by removing the formed trioxane from the reaction medium. This operation can be carried out according to any method well known to those skilled in the art, for example by withdrawal, and advantageously by distillation during the reaction.

As previously indicated, the trioxane can be withdrawn during the trioxane formation. According to another embodiment, the trioxane is withdrawn at the end of step 2), that is to say after the trioxane formation. The process according to the invention can be carried out batchwise or continuously. Particularly advantageously, when the process is carried out continuously, the trioxane is continuously withdrawn, throughout the reaction, as soon as it forms in the reaction medium. When the process is carried out batchwise, the trioxane is separated from the reaction medium during or at the end of step 2).

As previously indicated, the trioxane separation step can be carried out by any method known to those skilled in the art. According to one embodiment, the trioxane separation step is carried out by distillation. The distillation is, for example, simple distillation, fractional distillation, also called rectification, thin-film distillation, molecular distillation, or azeotropic distillation which can be carried out in the presence of a third solvent, generally an alcohol such as methanol or ethanol.

The distillation step can be followed by an additional step of purification, well known to those skilled in the art, using one or more of the following known methods: evaporation, filtration, extraction, distillation, recrystallization, and the like.

According to another embodiment, the step of separating the trioxane from the reaction medium comprises at least the following two substeps:
a) an extraction step advantageously carried out in the presence of an extraction agent;
b) and a distillation step in order to separate the trioxane and the extraction agent.

The extraction step a) is advantageously carried out in the presence of an extraction agent. An extraction agent is a compound which has low water-miscibility or is water-immiscible and which will entrain the trioxane with it. The extraction agent must dissolve the trioxane well. The extraction agents that can advantageously be used are organic solvents such as those chosen from benzene, methylene chloride, ethylene chloride, chloroform, cyclohexane, chlorobenzene, diethyl ether, and mixtures of two or more of them. Preferably, their boiling point is between 40° C. and 120° C.; preferably between 60° C. and 120° C.

The extraction step a) is followed by a distillation step b). The distillation may be simple distillation or fractional distillation, or any other distillation method already indicated above.

The distillation step b) may be followed by an additional separation step, such as an evaporation, a filtration, an extraction, a distillation, and the like.

According to a second aspect, a subject of the present invention is the use of a catalyst comprising methanesulfonic acid, for carrying out the trimerization of formaldehyde, in particular for preparing trioxane, more particularly trioxane by formaldehyde trimerization. According to one preferred embodiment, the catalyst employed for the use according to the present invention is methanesulfonic acid, and entirely preferably methanesulfonic acid in an aqueous solution.

A subject of the present invention is also the use of a catalyst comprising methanesulfonic acid for increasing the trioxane production yield, more particularly the yield from production of trioxane by formaldehyde trimerization. According to one preferred embodiment, the catalyst employed for the use according to the present invention is methanesulfonic acid, and entirely preferably methanesulfonic acid in an aqueous solution.

Finally, a subject of the present invention is the use of a catalyst comprising methanesulfonic acid for increasing the trioxane selectivity, more particularly the selectivity with respect to trioxane obtained by formaldehyde trimerization. According to one preferred embodiment, the catalyst employed for the use according to the present invention is methanesulfonic acid, and entirely preferably methanesulfonic acid in an aqueous solution.

The following examples illustrate the invention without limiting the scope thereof as conferred by the appended claims.

1,3,5-Trioxane synthesis tests are carried out by introducing, into a reactor, heated to 105° C., formaldehyde in solution at 60% in water and the acid catalyst which is either methanesulfonic acid, sold by the company Arkema (example according to the invention), or sulfuric acid (comparative example).

The 1,3,5-trioxane formed is extracted from the reaction medium and then purified by distillation. The results are indicated in table 1.

TABLE 1

| Reference | According to the invention | Comparative |
| --- | --- | --- |
| Formaldehyde | 60% aqueous | 60% aqueous |
| Catalyst | 5% MSA | 5% $H_2SO_4$ |
| Temperature | 105° C. | 105° C. |
| Time | 3 h | 3 h |
| Degree of formaldehyde conversion | 40% | 25% |
| Trioxane selectivity | 97.50% | 95% |

These results show that MSA allows a better degree of formaldehyde conversion, and a better 1,3,5-trioxane selectivity, compared with another strong acid catalyst: sulfuric acid.

The invention claimed is:

1. A process for the trimerization of formaldehyde to produce trioxane, comprising:
   (a) reacting formaldehyde in a reaction mixture comprising water, at least one protic organic solvent, or both, and no aprotic solvent, in the presence of a catalyst comprising at least methanesulfonic acid, to produce trioxane; and
   (b) separating the trioxane from the reaction mixture.

2. The process as claimed in claim 1, wherein the formaldehyde content ranges from 30% to 90% by weight, relative to the total weight of the reaction mixture, limits included.

3. The process as claimed in claim 1, wherein the content of methanesulfonic acid in anhydrous form or in an aqueous solution in the reaction mixture ranges from 0.1% to 25% by weight, limits included, of methanesulfonic acid expressed in anhydrous form, relative to the total weight of the reaction mixture.

4. The process as claimed in claim 1, wherein (a) is carried out at a temperature ranging from 0° C. to 200° C.

5. The process as claimed in claim 1, wherein (a) is carried out at a pressure set between $0.1 \cdot 10^5$ Pa and $10 \cdot 10^5$ Pa.

6. The process as claimed in claim 1, wherein the process is carried out continuously, with continuous withdrawal of the trioxane formed.

7. The process as claimed in claim 1, wherein the catalyst is methanesulfonic acid in an aqueous solution.

8. The process as claimed in claim 1, wherein the formaldehyde content ranges from 30% to 70% by weight relative to the total weight of the reaction mixture, limits included.

9. The process as claimed in claim 1, wherein the formaldehyde content ranges from 30% to 60% by weight relative to the total weight of the reaction mixture, limits included.

10. The process as claimed in claim 1, wherein the content of methanesulfonic acid in anhydrous form or in an aqueous solution in the reaction mixture ranges from 0.1% to 15% by weight, limits included, of methanesulfonic acid expressed in anhydrous form, relative to the total weight of the reaction mixture.

11. The process as claimed in claim 1, wherein the content of methanesulfonic acid in anhydrous form or in an aqueous solution in the reaction mixture ranges from 2% to 10% by weight, limits included, of methanesulfonic acid expressed in anhydrous form, relative to the total weight of the reaction mixture.

12. The process as claimed in claim 1, wherein (a) is carried out at a temperature ranging from 50° C. to 150° C.

13. The process as claimed in claim 1, wherein (a) is carried out at a temperature ranging from 70° C. to 140° C.

14. The process as claimed in claim 1, wherein (a) is carried out at a temperature ranging from 90° C. to 130° C.

15. The process as claimed in claim 1, wherein (a) is carried out at a pressure set between $0.1 \cdot 10^5$ Pa and $5 \cdot 10^5$ Pa.

16. The process as claimed in claim 1, wherein (a) is carried out at atmospheric pressure.

17. The process as claimed in claim 1, wherein the reaction mixture comprises water.

18. The process as claimed in claim 1, wherein the reaction mixture comprises at least one protic organic solvent.

19. The process as claimed in claim 1, wherein the reaction mixture comprises; water in the absence of organic solvent.

20. The process as claimed in claim 1, wherein the reaction mixture comprises water and wherein the water content of the reaction mixture is 10% to 70% by weight, limits included, relative to the total weight of the reaction mixture.

21. The process as claimed in claim 1, wherein the reaction mixture comprises water and wherein the water content of the reaction mixture is 30% to 70% by weight, limits included, relative to the total weight of the reaction mixture.

22. The process as claimed in claim 1, wherein the reaction mixture comprises water and wherein the water content of the reaction mixture is 50% to 70% by weight, limits included, relative to the total weight of the reaction mixture.

* * * * *